(12) United States Patent
Aubert et al.

(10) Patent No.: US 11,890,178 B2
(45) Date of Patent: Feb. 6, 2024

(54) ARTIFICIAL CONTRACTILE STRUCTURE

(71) Applicant: MYOPOWERS MEDICAL TECHNOLOGIES FRANCE SAS, Besancon (FR)

(72) Inventors: Christophe Aubert, Cudrefin (FR); Fabian Kaegi, Lausanne (FR); Francois Cabaud, Ecole Valentin (FR)

(73) Assignee: MYOPOWERS MEDICAL TECHNOLOGIES FRANCE SAS, Besançon (FR)

( * ) Notice: Subject to any disclaimer, the term of this patent is extended or adjusted under 35 U.S.C. 154(b) by 525 days.

(21) Appl. No.: 16/768,659

(22) PCT Filed: Nov. 30, 2017

(86) PCT No.: PCT/IB2017/001698
§ 371 (c)(1),
(2) Date: May 30, 2020

(87) PCT Pub. No.: WO2019/106402
PCT Pub. Date: Jun. 6, 2019

(65) Prior Publication Data
US 2021/0169626 A1    Jun. 10, 2021

(51) Int. Cl.
*A61F 2/00* (2006.01)
(52) U.S. Cl.
CPC ............ *A61F 2/0036* (2013.01); *A61F 2/005* (2013.01); *A61F 2210/0014* (2013.01); *A61F 2250/001* (2013.01)

(58) Field of Classification Search
CPC ...... A61F 5/005; A61F 5/0053; A61F 5/0063; A61F 5/0066; A61F 2/0036; A61F 2/004; A61F 2/0031
See application file for complete search history.

(56) References Cited

U.S. PATENT DOCUMENTS

| | | | |
|---|---|---|---|
| 6,432,038 B1 * | 8/2002 | Bakane | A61F 2/0036 600/29 |
| 2003/0144575 A1 | 7/2003 | Forsell | |
| 2010/0204803 A1 * | 8/2010 | Tozzi | A61F 2/0036 623/23.72 |
| 2010/0217071 A1 | 8/2010 | Ricol | |

(Continued)

*Primary Examiner* — Kaylee R Wilson
(74) *Attorney, Agent, or Firm* — CRGO Global; Steven M. Greenberg

(57) ABSTRACT

Artificial contractile structure (1) for a medical device, said artificial contractile structure (3) comprising: —an elongated member (3) adapted to contact a hollow body organ; —a closure (9) adapted to form the artificial contractile structure (1) into a closed loop around said hollow body organ; —a tension system (11) arranged to be connected to a control unit (28), said tension system (1) being adapted to modify an internal diameter of said closed loop in response to a force applied by said control unit (28). According to the invention, said elongated member (3) comprises a resilient core (5) and a biocompatible outer sheath (7). Said tension system (11) furthermore comprises a first tensile element (13) attached to a first point (3c) of said elongated member, and a second tensile element (15) attached to a second point (3d) of said elongated member, each of said tensile elements (15, 17) passing through an adaptor (17) situated between said first point (3c) and said second point (3d).

13 Claims, 6 Drawing Sheets

(56) References Cited

U.S. PATENT DOCUMENTS

| | | | |
|---|---|---|---|
| 2011/0071557 A1 | 3/2011 | Dlugos, Jr. et al. | |
| 2012/0053397 A1* | 3/2012 | Deegan | A61F 2/0036 600/30 |
| 2012/0095288 A1* | 4/2012 | Snow | A61F 5/005 600/37 |
| 2012/0184980 A1 | 7/2012 | Anderson | |
| 2013/0096586 A1* | 4/2013 | Tozzi | A61M 60/486 606/157 |
| 2015/0105859 A1* | 4/2015 | Frigstad | A61F 2/08 600/30 |
| 2016/0220341 A1* | 8/2016 | Anderson | A61F 2/004 |
| 2016/0367349 A1* | 12/2016 | Williams | A61F 2/0036 |

\* cited by examiner

ARTIFICIAL CONTRACTILE STRUCTURE

CROSS-REFERENCE TO RELATED APPLICATIONS

This application is a § 371 national phase entry of International Application No. PCT/IB2017/001698, filed Nov. 30, 2017, the entirety of which is incorporated herein by reference.

TECHNICAL FIELD

The present invention relates to the field of artificial sphincters, in particular, but not exclusively, for the treatment of urinary incontinence.

BACKGROUND ART

WO2015/117664 describes a form of mechanical artificial contractile structure proposed as an alternative to problematic hydraulic systems such as the AUS 800 marketed by American Medical Systems, Inc. The artificial contractile structure disclosed in the above-mentioned document comprises a flat strip arranged to be closed in a loop around the urethra (or any other hollow body organ) of a patient by means of a closure. Once applied to the hollow body organ, this latter can be constricted by means of tension applied by a wire passing through the structure of the strip. A series of lateral reinforcing elements are formed on outer side of the strip, which cause it to adopt a substantially U-shaped cross-section when said tension is applied, and thus to gently apply pressure to the organ.

In acute testing, this artificial contractile structure has shown promise in treating male incontinence, however it has certain drawbacks in treating the same condition in females, since its shape is insufficiently adapted to the female urethra. Indeed, the contractile structure disclosed in WO2015/117664 is designed to extend on both sides of the locking system when it is wound around the male urethra. When applying strength on the cable, the portion extending beyond the locking system present a lower resistance to contraction and would contract first, decreasing the efficiency of the cuff so designed. Whereas ways to strengthen this portion-so-called "dead zone" so that the contractile portion surrounding the urethra contracts in priority exist, they require additional devices and complicate the surgery. The present invention intent to remedy the situation.

Due to the female urethras being bigger than male urethras and their anatomical condition very different, the pulling distance needed to contract the structure may exceed the actual length of the structure disclosed in WO2015/117664 and, as such, may not achieve the intended pull distance required to make the patient continent again on the long term.

In addition, the sphincter muscle responsible for closing, respectively opening, the female urethra has a substantially U-shape (viewed in anatomical median plan), which only partially surrounds it. It is therefore contra-indicated to provide contraction forces about the full circumference of the female urethra as in the case of male patients, in particular under the urethra where the vagina wall is as this may possibly induce friction and erosion.

At the present time, the standard treatment of incontinence in female patients is by means of so-called slings, which are passive devices attached so as to apply pressure to the urethra, and thus to replace a certain amount of muscle function and thereby to restore continence. However, in long-term use, slings often fail as constant pressure of the slings on soft tissues leads to erosion or migration of slings through the urethra, thereby reducing the pressure applied to the urethra, and require placement of yet another sling. Indeed, some patients can undergo placement of several slings over time.

Due to the inadequacies of slings and limitations of hydraulic systems, there is a long-felt need for an improved system to better treat female incontinence.

DISCLOSURE OF THE INVENTION

An aim of the present invention is to overcome the above-mentioned drawbacks of the prior art, and thus to provide an artificial contractile structure particularly suitable for treatment of female incontinence. Although the artificial contractile structure of the invention is primarily intended for treatment of female incontinence, it can also be used in males, and may be used to constrict other hollow body organs such as blood vessels, ducts (such as the bile duct), the intestine, and so on.

This aim is attained by an artificial contractile structure for a medical device, as defined in claim 1. This artificial contractile structure, also known as a "cuff", comprises an elongated member, i.e. a long, relatively thin member which may be a strip of flat cross-section, or may have a more elaborate cross section such as a V or U shape or a corrugated shape, said elongated member comprising an elongated body extending a longitudinal direction between a first and a second end. Said elongated member is adapted to contact a hollow body organ such as a urethra around at least part of its circumference.

A tension system arranged to be connected to a control unit is also provided, said tension system being adapted to bring said first and second ends of the elongated body closer together in response to a force applied by said control unit so as to constrict the hollow body organ and thus form an artificial sphincter.

According to the invention, the elongated member comprises a resilient core and a biocompatible outer sheath, and the tension system comprises a first tensile element (such as a wire, cord, thread, tape or similar) attached to said first end of said elongated member, and a second tensile element (again such as a wire, cord, thread, tape or similar) attached to a second point of said elongated member. Each of said tensile elements passes through an adaptor situated on the elongated member between said first point and said second point.

This construction permits applying even, selective pressure to the hollow body organ, and is simple to position and adjust around a hollow body organ by laparoscopic surgery.

Advantageously, said resilient core comprises a lattice structure. This structure allows optimising the elasticity and the dimensions of the resilient core.

Advantageously, the resilient core comprises a shape memory alloy. These alloys typically have excellent elastic properties, and permit a particularly advantageous method of fabrication, disclosed below.

Advantageously, said first tensile element is attached at a said first end of said body of the elongated member, and said second tensile element is attached at a said second end of said of said body of the elongated member. The cuff thereby does not show any so-called "dead zone", or inactive portion.

Alternatively, said first tensile element may be attached at a first anchoring member arranged within the elongated member at said first end thereof, and said second tensile element may attached at a second anchoring member arranged within the elongated member at said second end of the body of the elongated member.

In an embodiment, said first and second anchoring members comprise a pivot means about which said first and second tensile element may slide in response to a force applied by said control unit so as to constrict the hollow body organ and thus form an artificial sphincter.

In embodiments, the first and second anchoring members may be integrally formed in said resilient core of the artificial contractile structure.

In embodiments, the artificial contractile structure may further comprise a closure adapted to form the artificial structure into a closed loop around said hollow organ. Preferably said closure then forms a link between said first and second ends of said elongated member.

In an embodiment, the artificial contractile structure may further comprise an arcuate self-supporting structure wherein said elongated member is installed, said self-supporting structure being configured for insertion on top of the circular striated muscle, thereby preventing dissection of the vaginal wall of a patient. Such configuration may be much favourable for implantation of female patients.

Advantageously, said closure may be integral with said elongated member, i.e. monobloc therewith, thereby resulting in a simple construction with a minimum number of pieces.

Advantageously, said tension system further comprises a flexible transmission attached pivotably to said elongated member, said first tensile element and said second tensile element passing through said flexible transmission. The flexible transmission can thus pivot with respect to the elongated member without kinking, which is useful not only in use, but also when being inserted into the patient by means of a trocar, since it can be easily folded up alongside the cuff. The cuff and the flexible transmission together constitute a medical device.

Advantageously, said flexible transmission is attached to an adaptor, said adaptor comprising at least one pulley around which said first tensile element and said second tensile element pass so as to enter into said flexible transmission. The one or more pulleys may be rotary or fixed, and serve to minimise friction with the tensile elements when they make the transition from the cuff into the flexible transmission.

Advantageously, a control system comprising an actuator is provided, said first tensile element and said second tensile element being attached to said actuator by means of an connector, said connector being attached to said actuator by means of a push-fit connection. Connection of the tensile elements and the flexible transmission to the actuator is thus simple, and does not require any rotation.

Advantageously, said push-fit connection comprises one or more coil springs and one or more O-ring linking a first annular groove provided in one of said actuator and said connector and providing a kinematic link with a further annular groove provided in another of said actuator and said connector. A particularly simple form of push-fit is thus proposed.

Advantageously, the connector comprises a connecting rod longitudinally movable within a coaxial plug, said connecting rod being attached to said tensile elements. Preferably, connecting rod comprises a crenelated part cooperating with releasable hooking members of said plug to allow locking of the connecting rod in said plug, whereas the connector is designed to disconnect automatically when a given force is reached, preventing harms to the patient, the crenelated portion also allows to disconnect the tensile element in any position of the rod without applying effort to the tensile element (this to protect the urethra from uncontrolled pull forces).

The aim of the invention is also attained by a method of manufacturing an artificial contractile structure as defined above, comprising steps of:
 forming said resilient core, thanks to the memory alloy that can be manufactured flat to ease the operations to follow (bending the guides for the tensile elements, overmolding, sheating, sleeving, etc.);
 applying said biocompatible sheath to said resilient core, for instance by overmoulding or sleeving on a pre-prepared sheath;
 assembling said closure and said tension system to said elongated member, either before or after applying said biocompatible sheath.

This method results in an artificial contractile structure presenting the advantages mentioned above.

Advantageously, the resilient core is formed from a shape memory alloy capable of adopting a first state and a second state, and hence exhibiting at least a one-way memory effect, the method comprising steps of:
 conforming said resilient core to be substantially flat in said first state, and to be curved in said second state, e.g. following an arc of a circle or oval, or following a horseshoe shape;
 causing said resilient core to adopt said first state, such as by bending it from its second state into said first state;
 applying said biocompatible sheath to said resilient core when said resilient core is in said first state;
 causing said resilient core to adopt said second state after application of said biocompatible sheath so as to impose a curvature on said elongated member, e.g. by heating it above the transition temperature of the material of the resilient core.

As a result, the artificial contractile structure can be assembled and its outer sheath can be applied in a flat state, which simplifies processing, and can then be caused to adopt the curved state beneficial for implantation in the patient without applying an external force which might damage the flexible elongated member.

Advantageously, the tension system is at least partially applied to said elongated member before said step of applying said biocompatible sheath to said resilient core. The tension elements can then pass through or under the outer sheath, Advantageously, the outer sheath applied by overmoulding onto said resilient core, resulting in a unitary construction without joints.

BRIEF DESCRIPTION OF THE DRAWINGS

The invention will be described below in connection with the appended drawings, which illustrate.

MODE(S) FOR CARRYING OUT THE INVENTION

Figure 1:
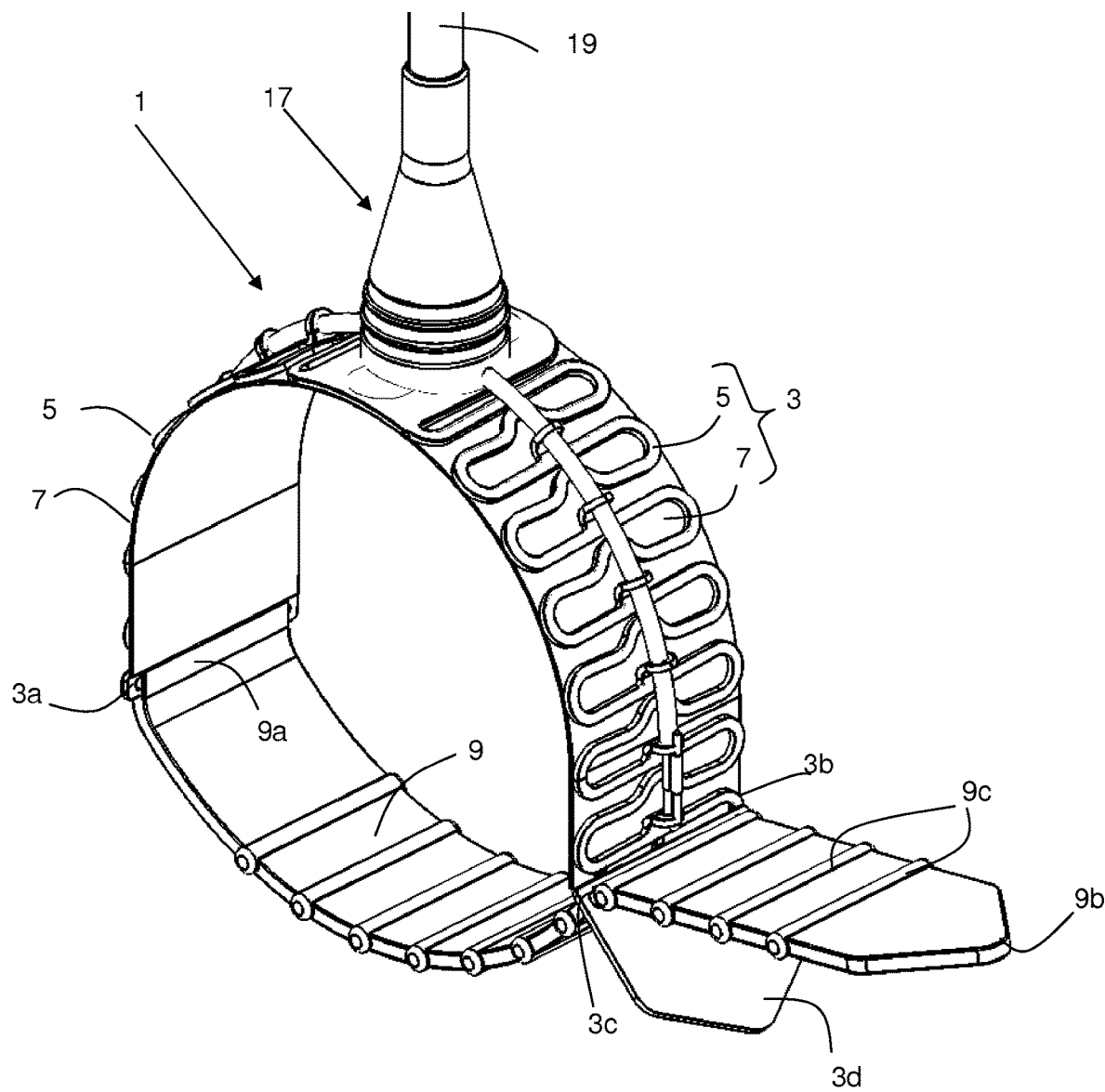
FIG. 1: a schematic, perspective transparent view of an artificial contractile structure according to the invention in a first embodiment.

FIG. 1 illustrates an artificial contractile structure 1 according to the invention. Such artificial contractile structures are often referred to as "cuffs", and this term will be used interchangeably with "artificial contractile structure" in the following description for ease of readability.

The cuff 1 comprises an elongated member 3, i.e. a long, relatively thin member which may be a strip of substantially flat cross-section or may have a V-shaped, U-shaped or corrugated cross-section (or similar), comprising a resilient core 5 and a biocompatible outer sheath 7. The elongated member 3 would typically be considered as being substantially flat, even if it comprises longitudinal corrugations or other similar structures; in other words, "flat" is not to be construed as being synonymous with "planar".

In the illustrated embodiment, the resilient core 5 is formed as a lattice of a resilient, elastic material such as a metal, however certain polymers such as SMPs (Shape Memory Polymers) are also suitable so as to give the elongated member 3 sufficient rigidity and flexibility. A shape memory alloy such as Nitinol is particularly suitable, for reasons which will be made clear below, although other metals are possible, such as titanium or stainless steel for instance. Although an oval lattice shape is shown in the figures, any other convenient shape of lattice (such as square, triangular, hexagonal or similar) is also possible, as is a solid ribbon of the resilient material. A typical thickness of the resilient core is 0.25 to 0.5 mm, and its width would typically be between 5 and 20 mm. However such dimensions shall be construed as limitative of the scope of the present invention.

The biocompatible outer sheath 7 may be formed as a hollow sleeve containing the resilient core 5, or may be overmoulded or laminated or dipped into a liquid silicone mixture to impregnate the stent onto the resilient core 5, and hence pass through the openings in the lattice structure of the resilient core 5 so as to form a unitary structure. The resilient core 5 may also be accommodated between two discrete sheets (halves) forming the outer sheath 7 when assembled together, Many suitable materials for the outer sheath are known in the field of implantable devices, such as biocompatible silicone, PTFE, and similar. The thickness of the outer sheath 7 should be sufficiently thin to be flexible, but sufficiently thick to act as a cushion and prevent the lattice structure, if present, from applying excessive pressure to the hollow body organ or hurting adjacent tissues. The skilled person is capable of carrying out the experimentation needed to determine the required thickness for a given structure of resilient core 5. In its resting, i.e. unstressed, position, the elongated member may follow a curve, e.g. an arc of a circle or oval, or a horseshoe shape, corresponding to the maximum diameter of hollow body organ intended for the cuff 1. This facilitates placing the cuff 1 around a hollow body organ, however, it is possible to supply such a cuff 1 with a flat resting shape.

Figure 2A:
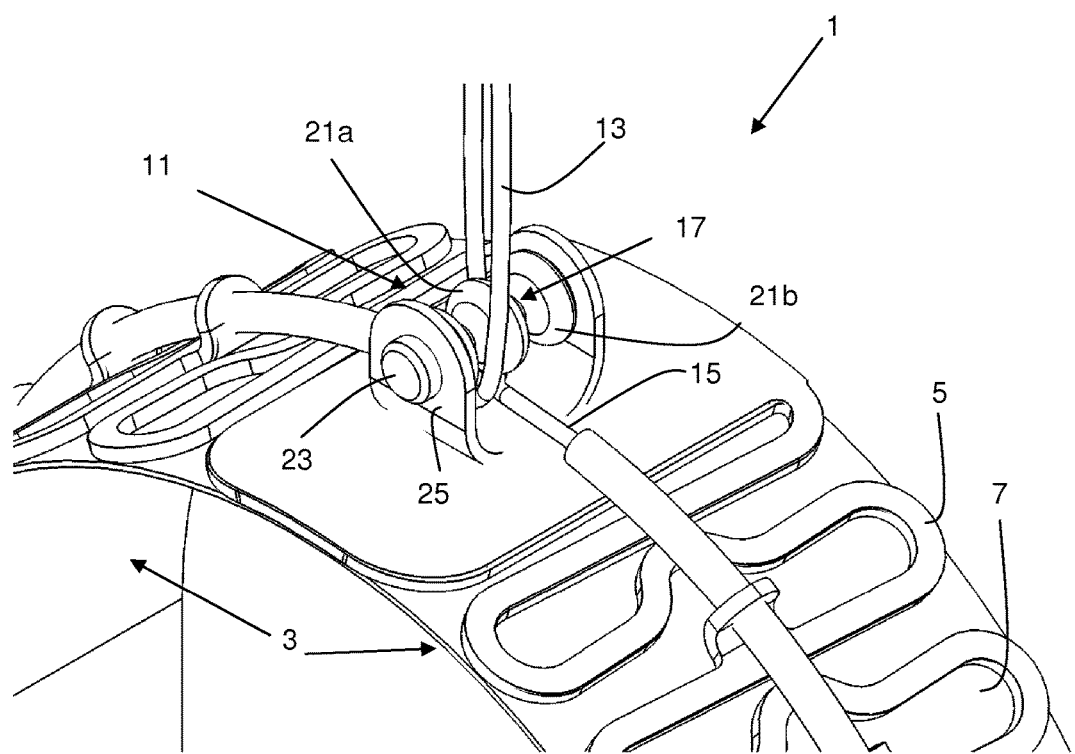
FIG. 2A: a schematic, perspective transparent view of the detail of a first embodiment of an adaptor forming part of the artificial contractile structure of FIG. 1.
Figure 2B:
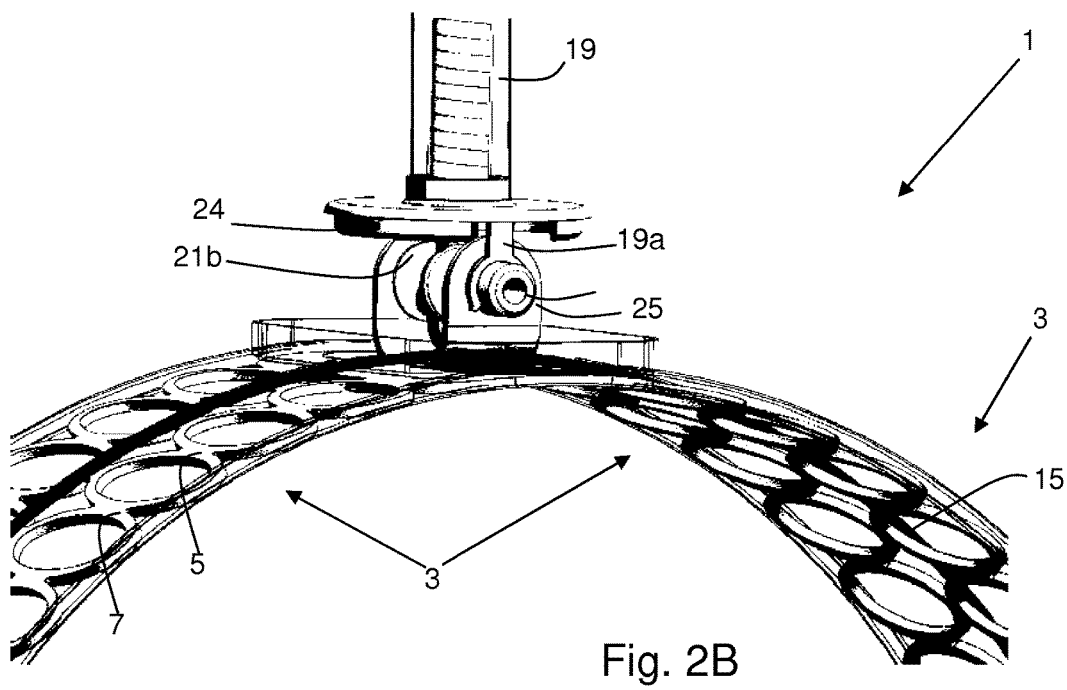
FIG. 2B: a schematic, perspective transparent view of the detail of a second embodiment of an adaptor forming part of the artificial contractile structure of FIG. 1.

Optionally, as represented in FIGS. 1 and 2, the artificial contractile structure 1 may comprise a closure band or strap 9. Such closure strap 9 may in some cases help forming the cuff 1 into a loop around a hollow body organ such as a urethra, blood vessel, intestine or similar. In the illustrated embodiment, the closure strap 9 is formed as a substantially loose ribbon or tape permanently attached at one end 9a to a first extremity 3a of the elongated member 3, its loose end 9b being arranged to pass through a suitable opening 3c in the elongated member 3, and to be retained therein. This opening 3c may be formed by a bar or loop of material integral with the resilient core 5, and/or integral with the outer sheath 7. Alternatively, a buckle arrangement may be provided as an additional piece fixed on, or integrated with, the second extremity 3b of the elongated member 3. Further alternately, the ribbon or tape may be a completely separate piece to the elongated member 3, and attached to each end thereof.

In order to secure the loose end 9b of the closure 9 at the desired point, a plurality of corrugations 9c are provided at intervals of e.g. 2.5 to 4 mm, so as to arrest the closure 9 at the desired point such that the cuff 1 has the desired circumference to conform to the hollow body organ of the patient around which it has been secured. Other forms of closure are also suitable. To help passing the end 9b of the closure strap 9 into the opening 3c arranged at the second end 3b of the elongated member 3 a holding tab 3d is advantageously provided as a free loose end of the outer sheath 7 of the elongated member, which advantageously help a surgeon firmly holding the end 3b of the elongated member while passing the closure strap end 9b in the opening 3c to set the closure 9 in place laparoscopically or otherwise. The closure 9 being devoid of any lattice structure may easily be cut after the proper adjustment has been found.

In order to cause the cuff 1 to constrict the hollow body organ, a tension system 11 is provided. This tension system 11, also represented in FIG. 2, comprises a first tensile element 13 secured at a first point at or proximate to the first extremity 3a of the elongated member 3, for instance by being tied, welded, glued or otherwise secured to a point at the end of the resilient core 5. The tension system 11 also comprises a second tensile element 15, again similarly secured at or proximate to the second extremity 3b and opening 3c of the elongated member 3. Ideally, the first and second tensile element 13, 15 are secured at the very ends 3a, 3b of the elongated member where the closure strap 9 attaches thereto, so as to minimise the so-called "dead zone" of the cuff, and to provide pressure on the hollow body organ over the greatest possible length of cuff 1.

The tensile elements 13, 15, may be wires, cords, threads, ribbons or similar. In practice, threads of braided Dyneema® (ultra-high-molecular-weight polyethylene), Aramid, or similar work well. They may pass through one or more tubes and/or longitudinal passages provided in the structure of the resilient core 5, or may pass around the outer side thereof either inside or outside of the outer sheath 7, for instance through one or more tubes. Also, first and second tensile elements 13, 15 may be two extremities of a single, unitary wire, cord, thread, ribbon or similar, or may be two distinct pieces. Since such tensile elements typically only work in tension, the inherent elasticity of the resilient core 5 and that of the underlying tissue causes the cuff 1 to relax once tension is removed from the tensile elements 13, 15 by the control unit 28 (see below). This is particularly advantageous as the failsafe state of the system is for the cuff is to reopen automatically to return the constricted hollow body organ to its naturally open position.

At a third point 3d intermediate between said ends 3a, 3b of the elongated member, an adaptor 17 is provided. This adaptor 17 serves to direct the tensile elements 13, 15 into a flexible transmission 19, which leads to a control system 28 (see FIGS. 4 and 5) arranged to apply tension to the tensile elements 13, 15, and to form a complete medical device. The flexible transmission 19 may be of any convenient type, such as a wire coil provided in an outer sheath, the tensile elements 13, 15 passing through an opening at the centre of this coil, and need not be described further. WO2015/117664 contains a discussion of various embodiments of such a flexible transmission, and is hereby incorporated in by reference in its entirety.

FIG. 2 illustrates in detail the adaptor 17, with its cover 17a removed.

The adaptor 17 serves to help the tensile elements 13, 15 make the transition from the elongated member 3 into the flexible transmission 19. In the illustrated embodiment, this is achieved by a pair of pulleys 21a, 21b, associated with the first tensile element 13 and the second tensile element 15 respectively, and around which the respective tensile element 13, 15 passes. The pulleys 21a, 21b are mounted rotatably or fixedly on an axle 23, itself mounted onto the resilient core 5 by means of a support element 25 fixed thereupon. Advantageously, the end of flexible transmission 19 is attached to the same axle 23, to allow it to pivot around the axis of the axle 23. As illustrated, the end of the flexible transmission 19 is provided with two parallel arms 19a (of which only one is visible) extending towards the axle 23 and terminating in "C"-shaped clips so as to clip onto the axle 23. These arms 19a bear a support platform 24 for transmission 19. Other arrangements, such as circular bearings, are also possible, but the illustrated variant is particularly simple and easy to assemble. This articulation of the flexible transmission 19 onto the cuff 1 is also particularly advantageous to permit folding the assembly formed of the cuff 1 and the transmission 19 into a trocar to permit insertion by laparoscopic surgery. This design is particularly suited for pulling perpendicular to the cuff 1. However, it may be in some instances convenient to pull transmission 19 substantially horizontally or more generally following a tangent to the cuff 1. In such case, the "pulleys" may advantageously be turned to 90° compared to FIG. 2.

Support element 25 may be rigidly fixed or integral with the resilient core, e.g. by laser soldering, or may be fixed so as to allow movement about at least one another axis so as to create a gimbal-type joint. For instance, the support element may be arranged to pivot according to an axis parallel to the longitudinal axis of the elongated member 3, and/or according to the axis perpendicular to the plane of the tangent of the elongated member 3 where it meets the adaptor 17. Such an arrangement helps to prevent kinking of the flexible transmission 19, and to permit it to be folded in a trocar.

In more simple embodiments, the tensile elements 13, 15 may simply pass through appropriately-placed passageways or around appropriately-placed surfaces, which may be provided with a low-friction surface such as highly-polished biocompatible metal, PTFE or similar. However, the use of pulleys 21a, 21b ensures that friction is kept to a minimum and a maximum of the force applied by the control unit (not illustrated) is applied to the cuff 1.

Figure 4A:
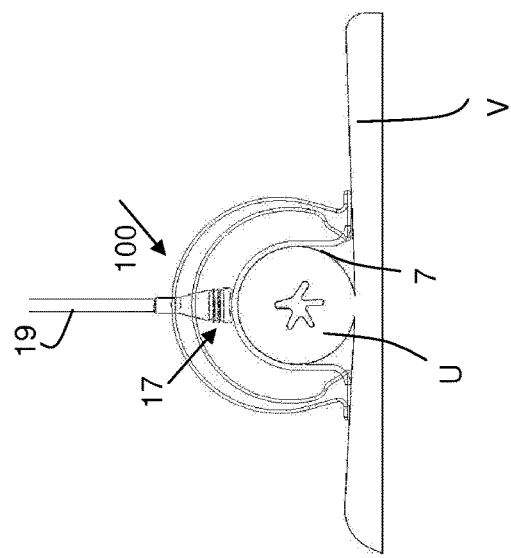
FIG. 4A to 4C: schematic cross-sectional views of the artificial contractile structure of FIG. 3 in different contracting positions about a female urethra.
Figure 4B:
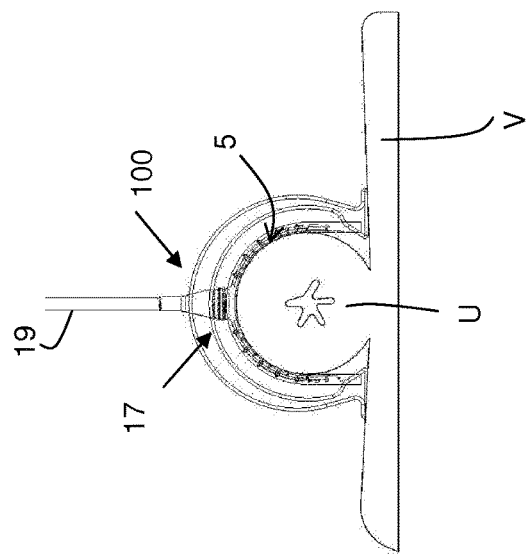
Figure 4C:
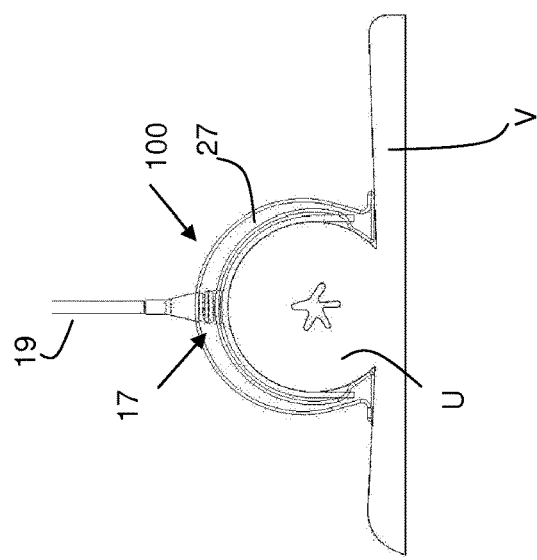
Figure 5:
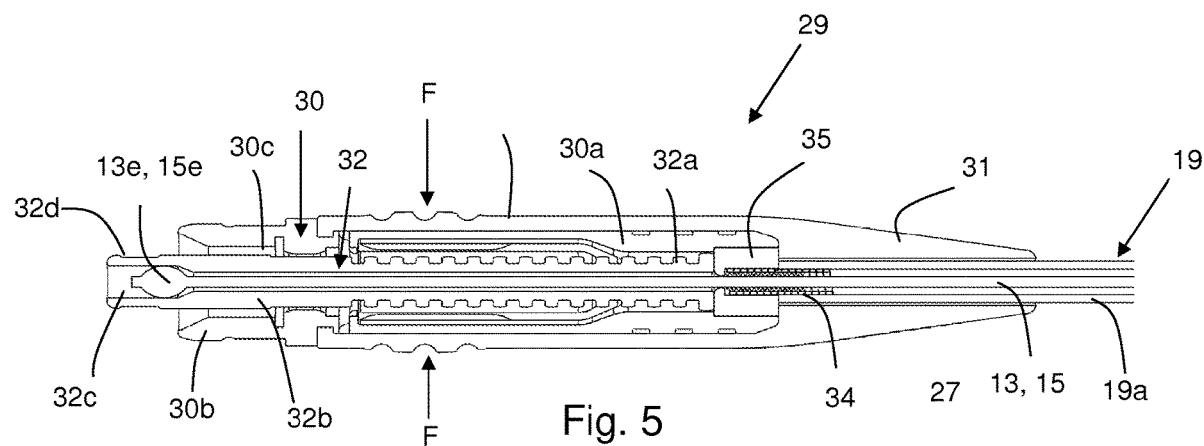
FIG. 5: a schematic cross-sectional view of a connector to a control system for an artificial contractile structure according to the invention.

A second embodiment of a cuff 100 specifically designed for female incontinence prevention is represented in FIGS. 3 to 5.

In that embodiment the cuff 100 shows an overall horseshoe shape, wherein an arcuate self-supporting structure 27 is adjusted over the elongated member 3, tension system 11 and adaptor 17. This horseshoe shape is specifically chosen for easing implantation of the cuff 1 about the circular striated muscle in order to compensate for weaknesses of said muscle, which is a main cause of female incontinence. As dissection of the vaginal wall is a risky procedure when trying to wrap a closing strap of the cuff 1 of FIG. 1, the horseshoe-shape cuff 1 of FIG. 3 is very appropriate for implantation of female patients.

The self-supporting structure 27 comprises an envelope 271 of a same material as the outer sheath 7 of the elongated member of the cuff of FIG. 1, which is tensioned or overmoulded on an arch 272 made of a substantially flexible polymeric rib 273, conforming two resting feet 274 for the arch to steadily rest against the vaginal wall V without hurting it.

Figure 3A:
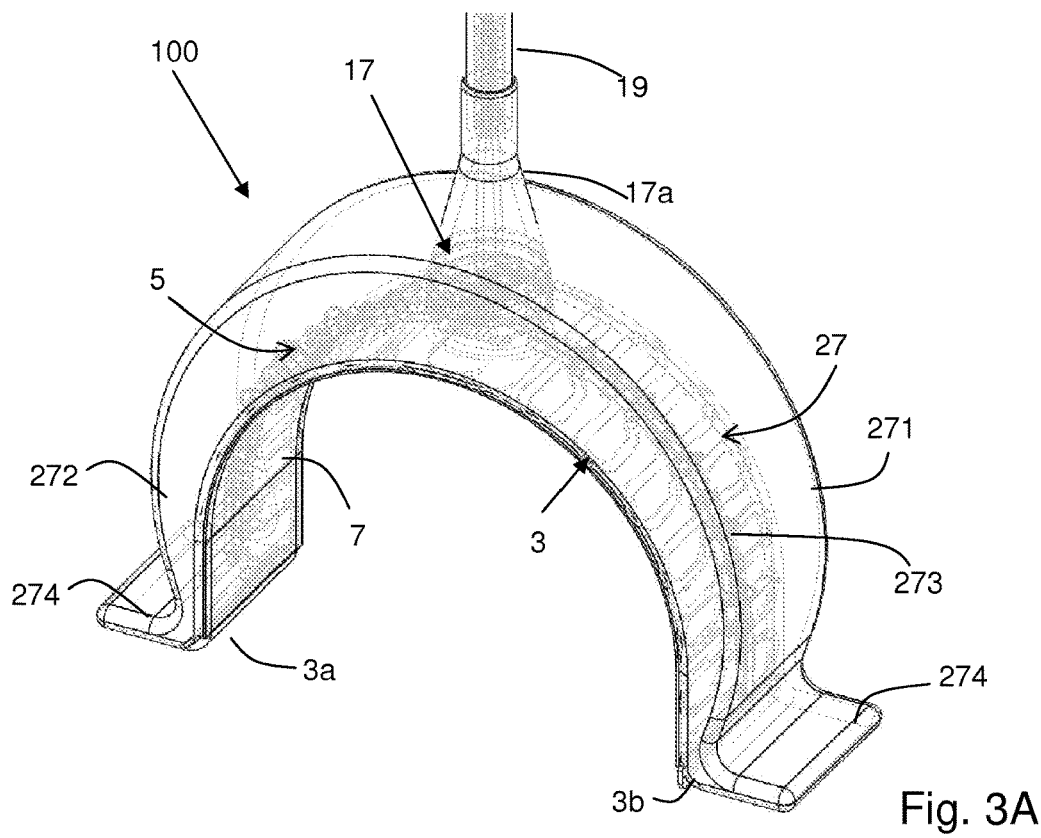
FIG. 3A: a schematic, perspective transparent view of an artificial contractile structure according to the invention in a first embodiment

The inner wall of the arch of the self-supporting structure 27, which is arranged for contacting a urethra U of a patient to provide contracting effort thereon is advantageously made of an elongated member 3, visible in shadow lining in FIG. 3A, similar in structure to the elongated member of the cuff 1 of FIG. 1, to the exception of an absence of closure strap 9, passing hole 3c and holding tab 3d. Depending on the materials used, the elongated member 3 may be glued or welded using heat, ultrasonic or high frequencies to the supporting structure 27.

The adaptor 17 and flexible transmission 19 remain identical to those described in relation to FIG. 1 and serve to transmit contractile force from an actuator to the tensile elements 13, 15 in order to constrict the elongated member 3 about the urethra of a patient as represent in FIGS. 4A to 4C, representing the shape evolution for the cuff 10 from a fully released position of the elongated member 3 to a contracted position thereof.

Figure 3B:
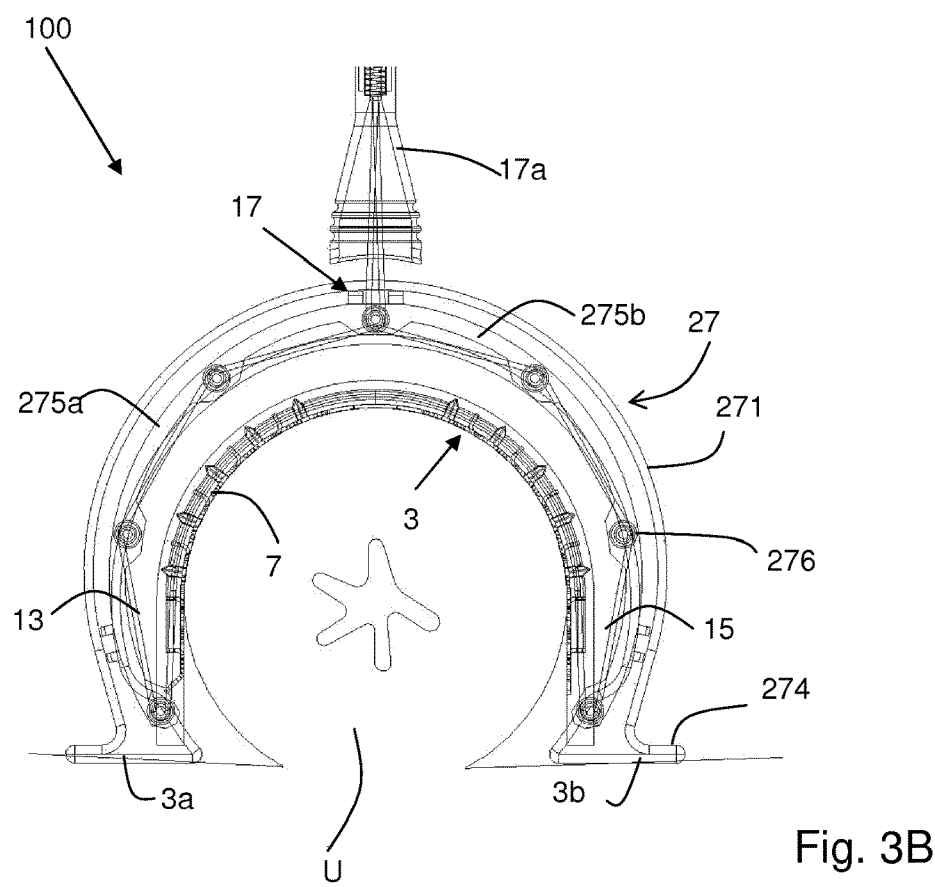
FIG. 3B: a schematic, cross-sectional view of an artificial contractile structure according to the invention in a second embodiment.

FIG. 3B represents an alternative embodiment of the cuff 100, wherein the self-supporting structure 27 comprises an arch 275 with two arms 275a, 275b supporting pulleys 276 about which the tensile elements 13, 15 are tensioned, the end of tensile elements 13, 15 joining on top of the elongated member 3. Thanks to that structure, the tensile efforts of the tensile elements 13, 15 are spread over the arms 275a, 275b supporting pulleys 276, for even constricting pressure on the urethra U.

Figure 6:
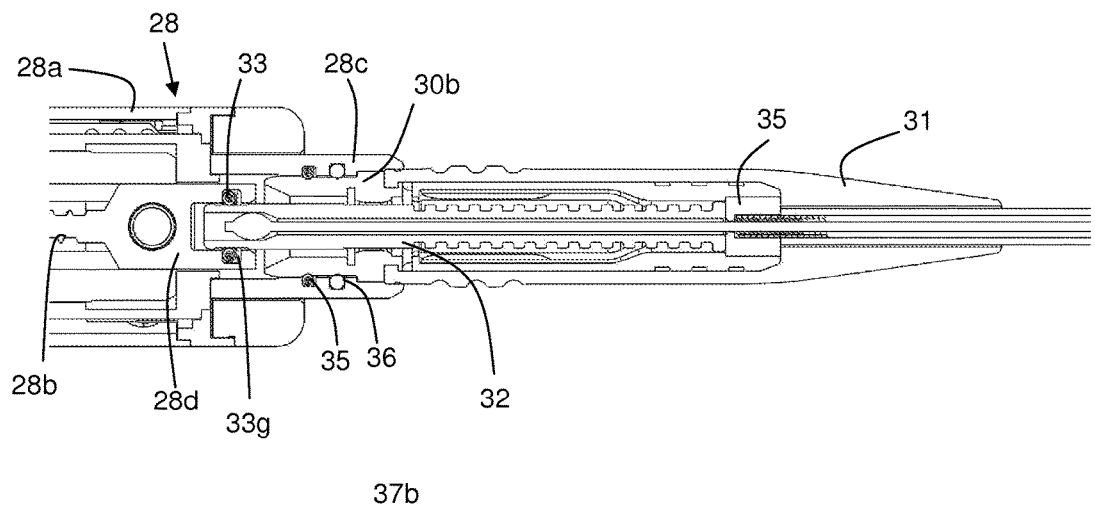
FIG. 6: a schematic cross-sectional view of the connector of FIG. 5 connected to a control system for an artificial contractile structure according to the invention.
Figure 7:
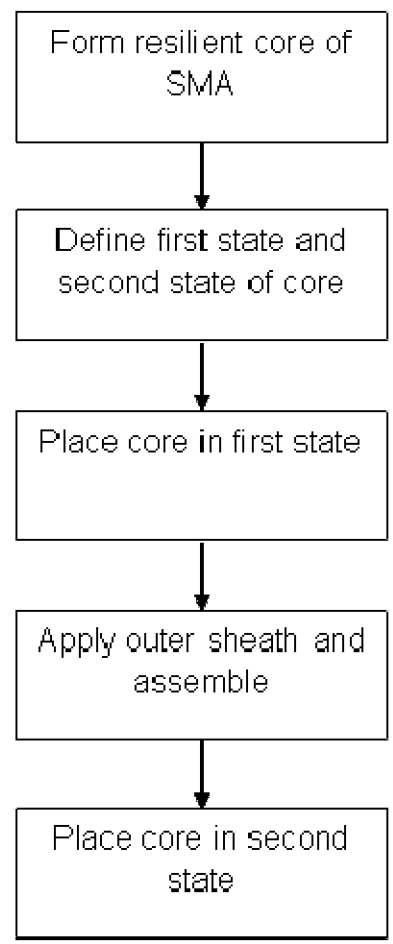
FIG. 7: a schematic flow diagram of a particularly advantageous method of manufacturing an artificial contractile structure according to the invention.

FIGS. 5 and 6 illustrate a push-fit connector system 29 for attaching the flexible transmission 19 comprising the tensile elements 13, 15 to a control system 28, such as a remotely operated actuator. It should be noted that the cuffs 1, 100 of the invention is however usable with any convenient control system.

The illustrated control system 28 comprises a housing 28a inside which a screw-type actuator 28b is mounted. Naturally, other types of actuator 28b are possible.

In order to simplify assembly of the entire system in situ, i.e. inside a body cavity of the patient, the attachment of the connector 29 to the control system 28 is carried out by means of push-fit joints, as will be explained in more detail below.

As illustrated in FIGS. 5 and 6, the tensile elements 13, 15 are formed from a single thread, an end 13e, 15e of which is secured to a plug 30. In FIG. 5, plug 30 comprises a substantially cylindrical body 30a, extending longitudinally within a cavity of a protective shell 31 made of biocompatible flexible material, in particular a silicon-based material for example, which can be overmoulded on the plug 30 and retained thereon by material insertion into recesses (not shown) arranged on the outer surface of the body. A plug head 30b extends outwardly from said body 30a outside the protective shell 31. The plug 30 has an open inner channel or tube 30c extending over the full length thereof, wherein a connecting rod 32 is fitted, said connecting rod comprising a crenelated part 32a housed in the plug's body 30a and a connecting head 32b extending through the plug's head 30b. Each tensile element 13, 15 is passed in a lumen or capillary in the connecting rod 32 and its end 13e, 15e, is preferably knotted to form a retention point received in an end recess 32c in the connecting head 32b. Tensile elements 13, 15 are thus fastened to the connecting rod 32, which will mechanically link the transmission 19 to the control system 28 as will be described herein after, Advantageously, the connecting rod 32 can translate within the plug 30 but that displacement is limited by the toothed configuration of the crenelated part, which engages with inner hooking members radially extending internally from the plug's body 30a. These hooking members can be actuated to engage the crenelated part by applying pressure as shown by arrows F in FIG. 5, thereby locking the connecting rod in place and allowing safe disconnection of the connector from the actuator without undue tension on the tensile elements The head 30bc of the plug 30 is cylindrical and is a sliding fit within a tube socket 28c extending from the housing of the control system. Upon insertion of the plug head 30b into the socket 28c the connecting head 32b attaches to a distal extremity 28d of the screw-type actuator 28b by any convenient attachment. In the illustrated embodiment, a first coil spring 33 held within a corresponding first annular groove 33g in the distal extremity 28d of the screw-type actuator 28b cooperates in a corresponding groove 32d arranged on the outer surface of the connecting head 32b. As an alternative, an O-ring may be used instead of a coil spring. Upon insertion of the connecting head 32b in the distal extremity 28d of the screw-type actuator 28b, the coil spring 35 clips into the annular groove 32d so as to retain the connecting head 32b and plug 30 upon the distal extremity of the screw-type actuator and to transmit force and movement thereto. In this sense, the coil spring provides a kinematic link between the connecting rod 32 and the distal extremity of the actuator. As a variation, the position of the two annular grooves 33g, 32d can be inverted if desired, the coil spring 33 thereby being supported in the connecting head 32b and clipping into the groove in the distal extremity 28d of the actuator.

In order to support the outer sheath 19a of the flexible transmission 19, a distal end of the protective shell 31 of the connector forms a hollow end cap fixed upon the outside of sheath 19a by means of a further coil spring 34 provided in between the tensile element 13, 15 and the sheath 19a on the one end and a seat 35 arranged between a distal end of the crenelated part 32a of the connecting rod 32 and the distal end of the cavity 30c. The tensile elements 13, 15 (see FIG. 4) pass through an axial passage in the seat 35.

In order to minimise ingress of fluid between connector 29 and the socket tube 28c, one or more coil spring(s) 35 and sealing rings 36 are provided in corresponding grooves in an inner wall of the socket tube 28c, in contact with the outer part of the plug head 30b.

The artificial contractile structure 1 of the invention can be manufactured by any convenient conventional manufacturing method, with the outer sheath 7 being either overmoulded or sleeved onto the resilient core 5, and the tension system assembled thereto at a convenient moment in the process. However, a particularly advantageous method of manufacture will be described below.

This method of manufacture applies when the resilient core 5 is constructed of a shape memory alloy such as Nitinol. In this method, the shape memory properties are not exploited to apply force to a hollow body organ when the cuff 1 is installed in a patient, but are exploited during its manufacture.

A summary of the main steps of this method is illustrated in FIG. 6.

In step 101, the resilient core 5 is formed of a shape memory alloy (SMA), such as nitinol, however other SMA's are also available and are suitable.

In this step, the resilient core 5 is formed in a substantially flat, planar configuration, e.g. by machining, deposition, extrusion (in the case of a solid strip) or similar. Since it is easier to work on a planar piece, this is significantly easier than forming the resilient core 5 with its final curvature already at this stage.

Since SMA's can present a one-way and/or a two-way memory effect, as is generally known, it is possible to define two shapes for the resilient core 5, and changing temperature above or below a transition temperature will cause the material to transition from one shape to another. Exploitation of a one-way memory effect is sufficient for this method, as will appear clearly below.

A simple way to exploit this effect is to bend the resilient core 5 to its desired final, curved, shape around a mandrel, while heating it above the material's transition temperature, thereby defining its "second state" ("second" being chosen here since it is the final shape adopted during manufacture, as will become clear below). This second state can have a form correspond to the maximum diameter of the hollow body organ around which the cuff 1 is intended to be placed, but may also be a different diameter, and may be formed into an arc of a circle or oval, or a horseshoe shape. The resilient core 5 can then be cooled to below the transition temperature, and bent back into a substantially flat configuration, defined as its "first state" (step 103).

Once the resilient core 5 has been placed in its first state by bending it out of its second state, assembly and application of the outer sheath 7 can occur (step 104). The adaptor 17, or at least part thereof such as support element 25, can be assembled thereto, and if the tensile elements 13, 15 are to pass through the structure of the resilient core 5 and/or under the outer sheath 7, these are then placed, and if desired attached at ends 3a, 3b of the elongated member 3. Otherwise, these can be attached later at an opportune moment. The outer sheath 7 is then applied to the resilient core 5, e.g. by overmoulding, or by sleeving a tube-shaped sheath thereupon. Overmoulding is the most advantageous process, since it results in a hermetically-sealed and encapsulated elongated member 3, in a single process step, and without seams or joints. Furthermore, the closure 9 can be formed integrally with the outer sheath 7 during such an overmoulding step, although it may be formed in a separate step and fixed to the elongated member 3 in any appropriate fashion.

If the tensile elements 13, 15 are not to pass underneath the outer sheath 7, they can be fixed after application of the outer sheath 7, i.e. in such a variant the assembly occurs after application of the outer sheath 7.

Once the cuff 1 is thus assembled, in step 105 the resilient core 5 is placed into (i.e. is caused to adopt) its second state, by heating it back up over the transition temperature of the SMA. The desired shape and curvature of the cuff 1 is hence obtained, and remains once the resilient core 5 cools back down below the transition temperature.

The cuff 1 is then ready for sterilisation, packaging and use.

Since the cuff 1 is provided with an appropriate curvature already, it is easier for the surgeon to place around the hollow body organ. A flat cuff is harder for the surgeon to handle laparoscopically, since it requires the surgeon to impose the desired curvature before he is able to close the closure 9.

One particular advantage of this method is that the curvature of the elongated member 3 does not need to be formed before applying the outer sheath 7, which would make assembly and application of the outer sheath 7 difficult. It also avoids having to bend the assembled cuff 1 into shape after assembly and after application of the outer sheath 7. Since the materials used for the resilient core 5 are elastic, in order to stress them sufficiently to obtain the required final shape by plastic deformation and yet retain sufficient elastic properties, high curvatures have to imposed thereon and heat may need to be applied. These curvatures (and heat, if applied), are likely to damage the outer sheath 7, reducing its integrity, and possibly delaminating it from the resilient core. This is not to say that such processes cannot be used to manufacture the cuff 1 of the invention, however they are not as adapted to its manufacture as the above-described method. Furthermore, if the cuff 1 is to be bent to fit into a trocar for insertion by laparoscopic surgery, the material of the resilient core 5 needs in any case to be capable of withstanding significant curvatures without undergoing plastic deformation, so any manufacturing method requiring plastically bending of the cuff 1 into its final shape after assembly is likely to be suboptimal.

In use, the cuff 1 is inserted into the patient by means of a trocar, an incision is made if necessary (depending on the hollow body organ around which the cuff 1 is being applied) so as to enable the elongated member 3 to be passed around the hollow body organ, and the closure 9 is closed and tightened to give the cuff 1 the desired diameter. Subsequently, the flexible transmission 19 and the first and second tensile elements 13, 15 are attached to the control module 28, e.g. as shown in FIG. 4 or 5.

Although the invention has been described in terms of specific embodiments, variations thereto are possible without departing from the scope of the invention as defined in the appended claims.

The invention claimed is:

1. An artificial contractile structure for a medical device, said artificial contractile structure comprising:
    an elongated member adapted to contact a hollow body organ, said elongated member comprising an elongated body extending a longitudinal direction between a first and a second end, the first and second end being arranged at a distance of one another on a first and second extremity, respectively, of the elongated member;
    a tension system arranged to be connected to a control unit, said tension system being adapted bring said first and second ends of the elongated body closer together in response to a force applied by said control unit, so as to constrict the hollow body organ;
    wherein said elongated member comprises a resilient core and a biocompatible outer sheath, and said tension system comprises a first tensile element attached to said first end of said elongated member, and a second tensile element attached to said second end of said elongated member, each of said tensile elements passing through an adaptor situated between said first end and said second end.

2. The artificial contractile structure according to claim 1, wherein said resilient core comprises a lattice structure.

3. The artificial contractile structure according to claim 1, wherein said resilient core comprises a shape memory alloy.

4. The artificial contractile structure according to claim 1, further comprising a closure adapted to form the artificial contractile structure into a closed loop around said hollow body organ, said first tensile element is attached at a first part of said closure, and said second tensile element is attached at a second part of said closure.

5. The artificial contractile structure according to claim 1, further comprising an arcuate self-supporting structure wherein said elongated member is installed, said self-supporting structure being configured for insertion between the circular striated muscle and the vaginal wall of a patient.

6. A medical device comprising an artificial contractile structure, comprising an elongated member adapted to contact a hollow body organ, said elongated member comprising an elongated body extending a longitudinal direction between a first and a second end, the first and second end being arranged at a distance of one another on a first and second extremity, respectively, of the elongated member, and tension system arranged to be connected to a control unit, said tension system being adapted bring said first and second ends of the elongated body closer together in response to a force applied by said control unit, so as to constrict the hollow body organ, wherein said elongated member comprises a resilient core and a biocompatible outer sheath, and said tension system comprises a first tensile element attached to said first end of said elongated member, and a second tensile element attached to said second end of said elongated member, each of said tensile elements passing through an adaptor situated between said first end and said second end;
    wherein said tension system further comprises a flexible transmission attached pivotably to said elongated member, said first tensile element and said second tensile element passing through said flexible transmission.

7. The medical device according to claim 6, wherein the control unit comprises an actuator, said first tensile element and said second tensile element each being attached to said actuator by means of connector, said connector being attached to said actuator by means of a push-fit connection.

8. The medical device according to claim 7, wherein said push-fit connection comprises a helicoidal spring or an o-ring linking a first annular groove provided in one of said actuator and said connector and providing a kinematic link with a further annular groove provided in another of said actuator and said connector.

9. The medical device according to claim 7, wherein the connector comprises a connecting rod longitudinally movable within a coaxial plug, said connecting rod being attached to said tensile elements.

10. The medical device according to claim 9, wherein connecting rod comprises a crenelated part cooperating with hooking members of said plug to allow locking of the connecting rod in said plug.

11. A method of manufacturing an artificial contractile structure comprising an elongated member adapted to contact a hollow body organ, said elongated member comprising an elongated body extending a longitudinal direction between a first and a second end, the first and second end being arranged at a distance of one another on a first and second extremity, respectively, of the elongated member, and tension system arranged to be connected to a control unit, said tension system being adapted bring said first and second ends of the elongated body closer together in response to a force applied by said control unit, so as to constrict the hollow body organ, wherein said elongated member comprises a resilient core and a biocompatible outer sheath, and said tension system comprises a first tensile element attached to said first end of said elongated member, and a second tensile element attached to said second end of said elongated member, each of said tensile elements passing through an adaptor situated between said first end and said second end, the method comprising the steps of:

- forming said resilient core;
- applying said biocompatible sheath to said resilient core; and,
- assembling said closure and said tension system to said elongated member, either before or after applying said biocompatible sheath.

12. The method according to claim 11, wherein said tension system is at least partially applied to said elongated member before said step of applying said biocompatible sheath to said resilient core.

13. The method according to claim 11, wherein said biocompatible sheath is applied by overmoulding onto said resilient core.

* * * * *